United States Patent [19]

Ikeda et al.

[11] Patent Number: 4,936,674

[45] Date of Patent: Jun. 26, 1990

[54] APPARATUS AND METHOD FOR DETERMINING FUNCTIONS OF CELLS

[75] Inventors: Yasuo Ikeda; Kiyotaka Sakai, both of Tokyo; Ichiro Itagaki, Kamakura; Masato Mikami, Kamakura; Shoji Nagaoka, Kamakura, all of Japan

[73] Assignee: Toray Industries, Inc., Tokyo, Japan

[21] Appl. No.: 334,575

[22] Filed: Apr. 7, 1989

[30] Foreign Application Priority Data

Apr. 8, 1988 [JP] Japan .................................. 63-87546

[51] Int. Cl.⁵ ...................... G01N 33/49; G01N 21/64
[52] U.S. Cl. .................................. 356/39; 250/459.1; 356/73; 356/427
[58] Field of Search ...................... 356/39, 40, 73, 340, 356/427; 250/459.1

[56] References Cited

PUBLICATIONS

Frojmovic, "Rheo-Optical Studies of Blood Cells," *Biorheology*, (1975) vol. 12, pp. 193-202.
O'Brien, "Platelet Aggregation," *J. Clin. Path.*, (1962) vol. 15, pp. 446-455.
Rieger et al, "An Improved Rheological Method...," *Thrombosis Res.*, vol. 17, (1980) pp. 589-593.
Klose et al, "A Rheological Method...,"*Thrombosis Res.*, vol. 7, (1975) pp. 261-272.
Salzman, "Measurement of Platelet Adhesiveness," *J. Lab. & Clin. Med.*, Nov. (1963), vol. 62, No. 5, pp. 724-735.
Born, "Aggregation of Blood Platelets...," *Nature*, Jun. 9, 1962, vol. 194, No. 4832, pp. 927-929.
Grynkiewicz et al, "A New Generation of $Ca^{2+}$ Indicators...," *J. Bio. Chem.*, (1985) vol. 260, No. 6, pp. 3440-3450.

*Primary Examiner*—Vincent P. McGraw
*Attorney, Agent, or Firm*—Birch, Stewart, Kolasch & Birch

[57] ABSTRACT

An apparatus for determining the functioning properties of cells which includes a sample containing chamber, a rotor disposed in the chamber and having a conical surface which faces the inner bottom surface of the chamber at an angle of not greater than 2°, a ray transmission path from which a ray is projected into a sample of a cell suspension between the rotor and the inner bottom surface, and a transmitted ray detection path from which transmittance from the sample is detected. The optical path length in the sample is not smaller than 1 cm. An adequate shear stress is applied to the sample by adjusting the gap between the rotor and the inner bottom surface and rotating the rotor. A fine response by the cells caused by the applied shear stress, particularly the aggregation of platelets in a platelet suspension, can be accurately and quantitatively determined with a high sensitivity.

27 Claims, 11 Drawing Sheets

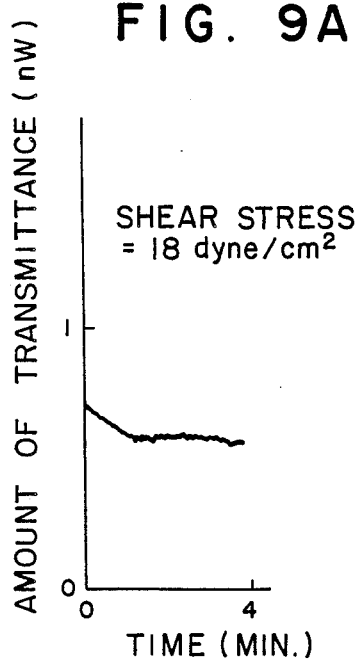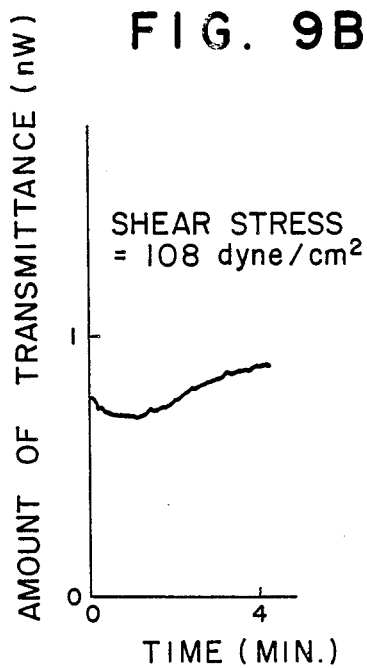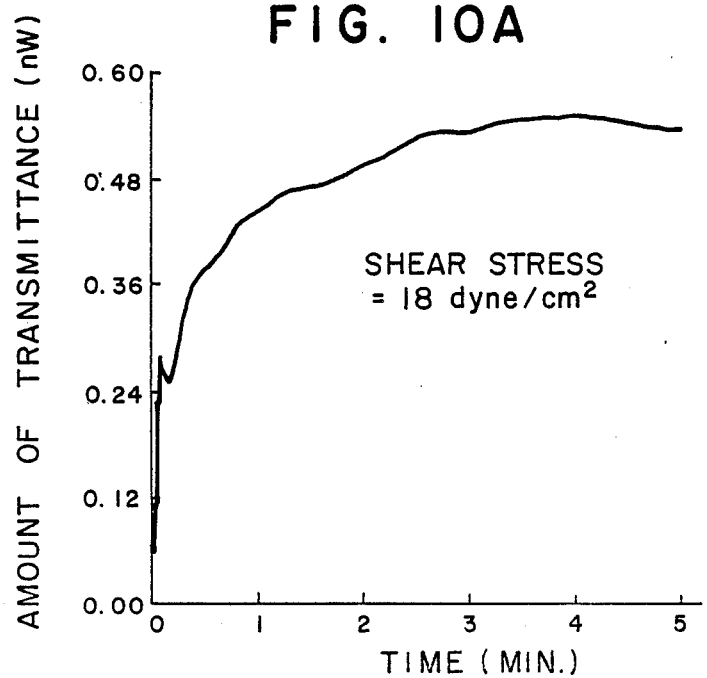

APPARATUS AND METHOD FOR DETERMINING FUNCTIONS OF CELLS

BACKGROUND OF THE INVENTION

1. Field of the Invention

The present invention relates to an apparatus and a method for determining the functioning properties of cells by measuring a fine response by the cells contained in a cell suspension when a shear stress is applied to the cell suspension. More particularly, the present invention relates to an apparatus and a method in which, for example, a shear stress is applied to a platelet suspension, and the fine aggregation of the platelets, the variation of the forms of the platelets and the release reaction of the platelets, etc. due to the applied shear stress are continuously measured with a high sensitivity. The present invention can be broadly used for diagnosis and treatment of congenital diseases such as thrombasthenia and von Willebrand disease and treatment of acquired diseases such as myocardial infarction, thrombosis and arteriosclerosis, which cause platelets to function abnormally. Further, an apparatus according to the present invention can be also utilized for development of medicines which are intended to treat platelet abnormalities.

2. Description of the Prior Art

Various apparatuses which determine the functioning properties of cells using a cell suspension have been developed. Particularly, the apparatus designed by Born and O'Brien (Born, G. V. R.: Nature, page 194, 927 (1962), and O'Brien, J. R.: J. Clin. Path. page 15, 446 (1962)) and the apparatus designed by Salzman (Salzman, E. W.: J. Lab. Clin. Med., page 62, 724(1963)) are known as apparatuses which can determine functioning properties of platelets, and these apparatuses are broadly used for clinical examinations.

The former apparatus (hereinafter called the first conventional apparatus) is used for examining the aggregation properties of platelets. This apparatus comprises an unit which includes a cylindrical glass container having the diameter of about 5 mm for measuring the transparency of a platelet suspension and a recorder which converts the measured transmittance to a corresponding electric signal and records the aggregation curve with a pen. In this apparatus, the platelet suspension of 0.2-0.3 ml which is separated from blood by a centrifugal separator is contained in a cylindrical glass container, and an aggregating agent such as adenosine diphosphate, collagen, epinephrine, ristocetin or thrombin is added to it. When the platelet suspension is stirred by a magnetic stirrer previously placed in the container, the platelets are rapidly formed into flocks and the measured transmittance of the platelet suspension increases. The variation of this transmittance can be continuously recorded as the aggregation curve of the platelets.

The latter apparatus (hereinafter called the second conventional apparatus) is used for examining the adhesive properties of platelets. This apparatus utilizes the characteristic of platelets for adhering to a glass surface. In this apparatus, blood is passed through a tube filled with glass beads, and the variation of the number of platelets before the passage as compared to after the passage is measured. The apparatus comprises a tube having an inner diameter of about 2 mm and a length of about 15 cm and filled with glass beads having a diameter of 0.3-0.4 mm and an empty tube for taking a sample of blood. The respective ends of the two tubes are connected to each other via a three-way cock having a needle for taking blood. Plastic syringes are connected to the respective unconnected ends of both the tubes. Further, an aspirator is connected to the two syringes, and blood is taken thereinto at a constant speed.

An academic publication reports the variation in properties of platelets caused when a shear stress of about 1 dyne/cm$^2$ is applied to a platelet suspension and is continuously recorded (Klose, H. J., Rieger, H. and Schid-Schonbein, H.: Thrombosis Res., page 7, 261 (1975)). An experimental apparatus (hereinafter called the third conventional apparatus) is disclosed in this report. The apparatus comprises a transmissible concave bath and a rotor having a conical surface facing the inner bottom surface of the bath at an angle of 3° and having a diameter of 5 cm. Two optical fibers are provided on the outer side surface of the bath for projecting a ray into the platelet suspension between the rotor and the inner bottom surface of the bath in the direction of the flow of the platelet suspension via one of the optical fibers and for detecting the transmitted ray from the inside of the bath via the second of the optical fibers. A halogen-lamp-stabilized light source is connected to the end of the optical fiber used for projecting the ray, and a photo detector connected to a recorder is connected to the end of the optical fiber used for detecting the transmitted ray.

Moreover, an apparatus which is improved over the third conventional apparatus (hereinafter called the fourth conventional apparatus) is reported (Rieger, H., Baier, H., Schroder, H., Wurzinger, L., Schid-Schonbein, H. and Blasberg, P.: Thrombosis Res. page 17, 589 (1980)). This fourth conventional apparatus has a structure, similar to a double cylinder type rotational viscometer, which comprises an inner cylinder having a light source and an outer cylinder rotatably provided around the inner cylinder. Although a double cylinder type rotational viscometer, generally, has a defect in that a secondary flow due to Taylor vortex is liable to occur, this defect is overcome in the fourth conventional apparatus by rotating the outer cylinder.

Furthermore, an apparatus similar to the third conventional apparatus (hereinafter called the fifth conventional apparatus) is reported (Frojmovic, M. M.: Biorheology, page 12, 193 (1975)). In this apparatus, an optical path length in a platelet suspension is reduced up to about 1 mm by disposing a light source and a photo detector in a direction perpendicular to the direction of the flow of the platelet suspension.

In the first conventional apparatus wherein functions of platelets are determined from the aggregation curve obtained by adding aggregating agents to the platelet suspension, there is a problem in that the stimulus applied to the platelets is not physiological. For example, in a clinical examination using this apparatus, the concentration of adenosine diphosphate in the platelet suspension is usually controlled from 2 $\mu$M to 10 $\mu$M, but it is unknown at all whether the adenosine diphosphate of such a high concentration causes the aggregation of platelets in an organism or not. Moreover, ristocetin which is one of the aggregation agents does not exist in an organism. Further, in spite of the fact that it is reported by many researchers that platelets are activated by the influence due to the flow of blood, the factor presenting the flow state of blood is defined only by the rotational speed of the stirrer which is generally not consistent and is not accurately determinable. Furthermore, since the optical path length in the platelet suspension is only about 5 mm, the variation of the amount of the transmitted ray due to a fine aggregation of the platelets in response to a fine stimulus in an organism cannot be detected. Thus, since the first conventional apparatus has the above problems, the results obtained by the apparatus do not accurately identify clinical symptoms at many times in spite of the broad use of the apparatus in clinical examinations.

In the second conventional apparatus wherein the adhesive characteristics of platelets for adhering to a glass surface is utilized, since the nonphysiological phenomenon of adhesion to a glass surface occurs, there are problems similar to those in the first conventional apparatus. Moreover, since the sample flows between glass beads in this apparatus, the flow state, which greatly influences the adhesive characteristics of platelets, is quite different from the flow state in an organism. Therefore, the results obtained by the apparatus frequently do not accurately represent the true properties of platelets.

On the other hand, the common characteristic of the third, fourth and fifth conventional apparatuses is that the flow state of a platelet suspension can be specified by shear stress which is a generic factor. Since the reactions of platelets play an important part in diseases such as myocardial infarction, thrombosis and arteriosclerosis, much research and many discussions have been conducted for many years as reported in many scientific and academic reports and documents, using these apparatuses and other apparatuses which can specify the flow state of a platelet suspension. Despite this fact, the third, fourth and fifth conventional apparatuses have not yet been capable for clinical examinations in comparison with the first and second conventional apparatuses. The reason is that, since the third, fourth and fifth conventional apparatuses have the following problems, the mechanism of the aggregation and reaction properties of platelets due to the shear stress has not been elucidated and the correlation between the aggregation and reaction of platelets and diseases has not been clarified.

First, the third conventional apparatus aims to measure the aggregation of platelets under the condition of a low shear stress such as about 1 dyne/cm$^2$ and uses a rotor having a conical surface which faces the inner bottom surface of the bath at an angle of 3°. Therefore, the uniform shear stress, which can be applied to the platelet suspension having a viscosity of about 1 centipoise by use of this apparatus, is about 5 dyne/cm$^2$ at the highest. When a shear stress higher than the above value is applied to the platelet suspension, the flow state of the suspension becomes turbulent, and the applied stress becomes nonuniform. Moreover, in this apparatus, since the light having a broad wave length distribution emitted from a halogen lamp light source is projected into the platelet suspension without use of an optical filter or a spectroscope, the transmittance of the rays that are detected is liable to be influenced by the absorption of the rays due to the protein in the blood and/or the scattering of the rays due to the lipid in the blood. Furthermore, the relationship between the size of the particles and the scattering of light varies in a complicated manner according to the wave length of the light in a big particle dispersion system such as a platelet suspension. Therefore, when the light having such a wave length distribution is directly projected into the platelet suspension, a fine aggregation of the platelets due to the shear stress cannot be detected. The fourth conventional apparatus improves the defect of the third conventional apparatus by reducing the optical path length by using a structure of double cylinders. In this apparatus, however, since the optical path length is almost the same as or smaller than that in the first conventional apparatus, a large aggregation of the platelets can be measured, but a fine aggregation of the platelets due to a very small physiological stimulus cannot be measured.

The optical path length in the fifth conventional apparatus is very small, i.e. about 1 mm. Therefore, this apparatus is quite unsuitable for measuring a fine variation of platelets.

SUMMARY OF THE INVENTION

An object of the present invention is to provide an apparatus and a method which can continuously measure a fine response by cells in a cell suspension when a shear stress is appled to the cell suspension, particularly which can continuously measure a fine reaction by platelets in a platelet suspension when a shear stress is applied to the platelet suspension, and which can be used for diagnosis and treatment of diseases which cause variations in the functions of platelets and can be utilized for development of medicines intended to treat platelet abnormalities.

To accomplish the above object, an apparatus for determining the functioning properties of cells which are contained in a sample of a cell suspension, according to the present invention, comprises a sample containing chamber cylindrically defined by an inner bottom surface and an inner side surface, a rotor disposed in the sample containing chamber and having a conical surface convex toward the inner bottom surface of the sample containing chamber, a ray transmission path provided on the inner side surface of the sample containing chamber which provides for the transmission of a ray through the sample located between the inner bottom surface of the sample containing chamber and the conical surface of the rotor, and a transmitted ray detection path provided on the inner side surface of the sample containing chamber which provides for the detection of a ray transmitted through the sample located between the inner bottom surface of the sample containing chamber and the conical surface of the rotor. The conical surface of the rotor faces the inner bottom surface of the sample containing chamber at an angle of not greater than 2°. The optical path length in the sample between the ray transmission path and the transmitted ray detection path is not smaller than 1 cm.

The apparatus may further comprise a driving means connected to the rotor for rotating the rotor, a control unit for controlling the driving means, a light source operatively connected to the ray transmission path for supplying rays thereto, a photo detector operatively connected to the transmitted ray detection path for detecting the transmitted ray therefrom, and a recorder connected to the photo detector for recording a signal sent from the photo detector.

The sample containing chamber may be defined by a cylindrical bath constructed of a light-transmissible side wall and a bottom wall.

A method for determining the functioning properties of cells which are contained in a sample of a cell suspension, according to the present invention, comprises the steps of placing a sample into a sample containing chamber which is cylindrically defined by an inner bottom surface and an inner side surface, applying a shear stress to the sample located between the inner bottom surface of the sample containing chamber and a conical surface of a rotor disposed in the sample containing chamber by rotating the rotor, projecting a ray from the inner side surface to the sample located between the conical surface and the inner bottom surface so as to maintain an optical path length of the projected ray in the sample at a length of not smaller than 1 cm, detecting the ray transmitted through the sample from the inner side surface, and determining the degree of aggregation of the cells contained in the sample, which is caused by applying the shear stress, by measuring the variation of the transmitted ray detected from the inner side surface. The conical surface of the rotor is convex toward the inner bottom surface of the sample containing chamber and faces the inner bottom surface at an angle of not greater than 2°.

The properties of cells determined by the present invention are the reactions by cells caused directly or indirectly by the applied shear stress, and more concretely, the aggregation properties of the cells, the release of substances from cells and the variations of the forms of cells, etc.

In the apparatus according to the present invention, a shear stress is generated in the sample between the rotated rotor and the inner bottom surface of the sample containing chamber. The gap between the rotor and the inner surface of the sample containing chamber must be set such that the shear stress generated between the outer side surface of the rotor and the inner side surface of the sample containing chamber may not be greater than the shear stress generated between the conical surface of the rotor and the inner bottom surface of the sample containing chamber. If the inner diameter of the sample containing chamber is excessively large, the amount of the sample to be contained into the chamber also becomes large, and thus an excessive large inner diameter is not preferable. The inner diameter of the sample containing chamber is preferably set so that the gap between the outer side surface of the rotor and the inner side surface of the sample containing chamber may be 0.2–2.0 mm.

The sample containing chamber is desirably defined by a cylindrical bath which has a light-transmissible side wall and which is constructed so as to be separable from a holder that holds the bath. Since the bath can be detached from the holder, it is easy to handle the bath or to place the sample into or take the sample out from the bath. The bottom wall of the bath is preferably non-light-transmissible, because more precise data can be obtained with this construction. When the cylindrical bath is used, the gap between the outer side surface of the rotor and the inner side surface of the bath is also preferably set to 0.2–2.0 mm. At least the portions of the side wall of the bath which contact the ray transmission path and the transmitted ray detection path must be light-transmissible. For example, when the transmitted ray is in the visible area of the spectrum, the preferable material of the side wall is a plastic material such as an inexpensive acrylic polymer or polystyrene, and when the transmitted ray is in the ultraviolet or infrared area of the spectrum, quartz glass is desirable for the material.

In the apparatus according to the present invention, the radius of the rotor which applies a shear stress to the cell suspension is preferably not greater than 3 cm, more preferably in the range of 0.7–2.0 cm. The inner bottom surface of the sample containing chamber extends perpendicular to the rotational axis of the rotor. The angle between the conical surface of the rotor and the inner bottom surface of the sample containing chamber is not greater than 2°, and is preferably in the range of 0.3°–1.5°.

In the apparatus, optical fibers are desirably used in the ray transmission path and the transmitted ray detection path, respectively. As the material for the optical fibers, an inexpensive plastic is desirable when the ray is in the visible area of the spectrum, and quartz glass is desirable when the ray is in the ultraviolet or infrared area of the spectrum.

The light source operatively connected to the ray transmission path is selected in accordance with the characteristic of the cells to be measured. A halogen lamp or tungsten lamp to which an interference filter is attached, or an emitter which can emit a ray having a high monochromatic characteristic such as laser, is preferable as the light source. Two or more kinds of light sources may be used at the same time, and the rays emitted from these sources may be transmitted by the optical fiber in the ray transmission path.

In the apparatus according to the present invention, a detector utilizing a photoelectromotive force, such as a photodiode, is desirable as the photo detector. In a case where the ray to be detected is a weak ray such as a fluorescent ray, a photomultiplier is preferably used for the photo detector. When two or more kinds of rays are emitted, or when two or more kinds of fluorescent rays are detected, it is desirable to transmit only the ray or rays to be detected which have objective wave lengths by using optical filters such as interference filters and to transmit the respective selected rays to the photo detector via an optical fiber.

In the present invention, the optical path length is defined as the shortest distance between the ray transmission path and the transmitted ray detection path in the cell suspension in the sample containing chamber. This optical path length must be not smaller than 1 cm. The optical path length is preferably in the range of 1–4 cm, more preferably 2–3 cm. The locations of the ray transmission path and the transmitted ray detection path are desirably designed so that a hypothetical line between the paths does not pass through the rotational center of the rotor and so that the optical path length is as long as possible.

In the apparatus according to the present invention, the distance between the inner bottom surface of the sample containing chamber and the conical surface of the rotor is desirably adjustable. For example, the tip portion of the conical surface of the rotor is constructed from a magnetic material, a sensor of an eddy-current displacement gauge is provided in a bottom wall of the sample containing chamber, and the distance is detected by the sensor. Moreover, a columnar magnetic material constructed from, for example, stainless steel may be provided on the tip portion of the conical surface of the rotor in order to make it easy to measure the distance.

In a case where the variation of the forms of platelets or the variation of the concentration of calcium ions in platelets is determined by the apparatus according to the present invention, a scattered ray transmission path is desirably provided on the inner side surface of the sample containing chamber. The variation of the concentration of calcium ions in platelets is determined by measuring the fluorescence from the sample as described later. In the determination of the variation of the forms of platelets, desirably, the shear stress applied to the sample is set to be not greater than 10 dyne/cm², or a platelet aggregation inhibitor such as prostaglandin is added to the sample.

In the apparatus according to the present invention, the driving means for rotating the rotor desirably comprises a direct current motor with an encoder. A large and uniform shear stress up to 200 dyne/cm² can be sufficiently applied to the sample by use of such a driving means. The drive of the driving means is controlled by a control unit. When a program can be stored in memory in the control unit, the rotor can be driven not only at a constant rotational speed but also so as to apply various shear stresses to the sample of a cell suspension in the broad range from 0 dyne/cm² to 200 dyne/cm² in a single measurement and so as to determine the reaction of cells in the sample in the broad range in a single measurement.

In the present invention, the abnormalities of the glycoprotein on the cell membrane of platelets and the plasma protein combining with the glycoprotein, which are closely connected with the functions of platelets, can be easily investigated by determining the aggregation of platelets in the low range of 10–40 dyne/cm² and the high range of not smaller than 80 dyne/cm² in shear stress. Namely, in the apparatus according to the present invention, since a shear stress which is a physiological and a fine stimulus is applied to cells and a fine variation of the cells in response to the stimulus can be measured with a high sensitivity, the following phenomena can be discovered with respect to the functioning of platelets.

Although much research with respect to the functions of platelets have been reported, most of the mechanisms of the functions have not been made clear. The relationship between shear stress applied to a sample of a platelet suspension and the aggregation of the platelets due to the applied shear stress is examined in the range of the shear stress of 0–200 dyne/cm², using the apparatus according to the present invention. As a result, it becomes clear that the aggregation of platelets is closely connected with the glycoprotein (hereinafter also called "GP") on the cell membrane of platelets and the plasma protein combining with the glycoprotein, and that the mechanism of the aggregation caused in the range of 10–40 dyne/cm² is different from the mechanism of the aggregation caused in the range of not smaller than 80 dyne/cm². Presently more than ten types of GP are known, and it is reported that these GPs are closely connected with the functions of platelets such as aggregation and adhesive properties. Particularly, it is reported that, among these GPs, GPIb is connected with the adhesive properties of platelets and the complex of GPIIb and GPIIIa (hereinafter called "GPIIb/IIIa") is connected with the aggregation properties of platelets. On the other hand, with respect to the plasma protein, the von Willebrand factor is closely connected with the adhesive properties of platelets and fibrinogen is closely connected with the aggregation properties of the platelets, respectively.

First, the relationship between the glycoprotein on the cell membrane of the platelets and the aggregation of the platelets due to the applied shear stress is analyzed. As a result, the following facts are made clear. As shown in detail in Example 2 described later, when a platelet suspension is treated with monoclonal antibody of GPIb, the aggregation of platelets is promoted in the range of 10–40 dyne/cm² of shear stress, and it is completely suppressed in the range of not smaller than 80 dyne/cm². When a platelet suspension is treated with monoclonal antibody of GPIIb/IIIa, the aggregation of platelets is completely suppressed in the range of 10–40 dyne/cm² of shear stress, and it is incompletely suppressed in the range of not smaller than 80 dyne/cm². Further, in the sample taken from a patient of Bernard-Soulier syndrome in which GPIb is lacking, platelets normally aggregate in the range of 10–40 dyne/cm² of shear stress, but platelets do not aggregate at all in the range of not smaller than 80 dyne/cm². In the sample taken from a patient of thrombasthenia in which GPIIb/IIIa is lacking, platelets do not aggregate at all in the range of 10–40 dyne/cm² of shear stress, but platelets slightly aggregate in the range of not smaller than 80 dyne/cm².

Next, the relationship between the plasma protein and the aggregation of platelets due to the applied shear stress is analyzed. As a result, also as shown in detail in Example 2, when a platelet suspension is treated with monoclonal antibody acting against combining portions of GPIIb/IIIa of von Willebrand factor, the aggregation of platelets is not suppressed at all in the range of 10–40 dyne/cm², but it is completely suppressed in the range of not smaller than 80 dyne/cm². In the sample taken from a patient suffering from von Willebrand disease in which von Willebrand factor is lacking, platelets normally aggregate in the range of 10–40 dyne/cm² of shear stress, but platelets do not aggregate at all in the range of not smaller than 80 dyne/cm². In the sample taken from a patient suffering from afibrinogenemia in which fibrinogen is lacking, platelets do not aggregate at all in the range of 10–40 dyne/cm² of shear stress, but platelets normally aggregate in the range of not smaller than 80 dyne/cm².

Thus, as the result of this research by the use of the apparatus according to the present invention, it becomes clear that two mechanisms occur in the aggregation of platelets due to the application of shear stress.

Namely, the aggregation of platelets caused in the range of low shear stress of 10–40 dyne/cm² is connected with the combination of fibrinogen which is a plasma protein and GPIIb/IIIa which exists on the membrane of platelets, due to their mutual action. The aggregation of platelets caused in the range of high shear stress of not smaller than 80 dyne/cm² is connected with the combination of von Willebrand factors, which are plasma protein, due to GPIb and GPIIb/IIIa. These important discoveries provide a simple and accurate method for determining the aggregation properties and the adhesive properties of platelets which are two important functions of platelets. That is, by measuring the aggregation of platelets caused by applying shear stress to the sample, the aggregation properties of platelets can be determined in the range of 10–40 dyne/cm² and the adhesive properties of platelets can be determined in the range of not smaller than 80 dyne/cm², respectively.

The above aggregation of platelets can be accurately and continuously determined by using the apparatus according to the present invention. A fine response to stimulation by cells can be determined as well by the apparatus of the present invention. A sample of a cell suspension (a platelet suspension) is contained in the sample containing chamber, the rotor is rotated, and a shear stress is applied to the sample located between the conical surface of the rotor and the inner bottom surface of the sample containing chamber. A ray is transmitted into the sample located between the conical surface and the inner bottom surface from the ray transmission path, the transmitted ray is detected from the transmitted ray detection path and the transmitted ray is continuously detected and recorded. The fine response by the cells to the uniformly applied shear stress at the state of laminar flow, particularly the aggregation of platelets, is continuously determined by measuring the variation of the transmitted ray, i.e. the variation of transmittance.

The fine response by the cells can be determined with a high sensitivity of about 1000 times that of the conventional apparatus, particularly abnormalities associated with glycoprotein and plasma protein which are closely connected with the functions of the platelets can be determined easily and accurately. Accordingly, the apparatus and method according to the present invention can be used for diagnosis and treatment of diseases which cause platelets to function abnormally, and also can be utilized for development of medicines which are intended to treat platelet abnormalities.

Furthermore, the apparatus according to the present invention can be used for determining the variation in concentration of calcium ions in the cytoplasm of platelets. This concentration of calcium ions is important with regard to controlling the functions of a platelet suspension. For example, a pigment, such as Indo-1AM (Grynkiewicz, G., Poenie, M. and Tsien, R. V.: J. Biol. Chem., page 260, 3440 (1986)), which can easily permeate through the cell membrane, accumulates in the cytoplasm and can emit a fluorescence by combining with calcium ion, is added to the sample of a platelet suspension. A ray including an excitation light for the pigment is projected to the sample and the fluorescence from the pigment which is generated by the excitation light is continuously detected. Thus, the variation of the concentration of calcium ions in the cytoplasm of platelets can be continuously determined by measuring the variation of the detected fluorescence.

BRIEF DESCRIPTION OF THE DRAWINGS

The above and other objects, features and advantages of the present invention will become apparent and more readily appreciated from the following detailed description of the preferred exemplary embodiments of the invention, taken in conjunction with the accompanying drawings, in which:

FIGS. 9A and 9B are graphs showing still further amounts of transmittance measured in Example 2 using the apparatus shown in FIG. 1;

FIGS. 10A and 10B are graphs showing yet further amounts of transmittance measured in Example 2 using the apparatus shown in FIG. 1;

DETAILED DESCRIPTION OF THE PREFERRED EMBODIMENTS

Figure 1:
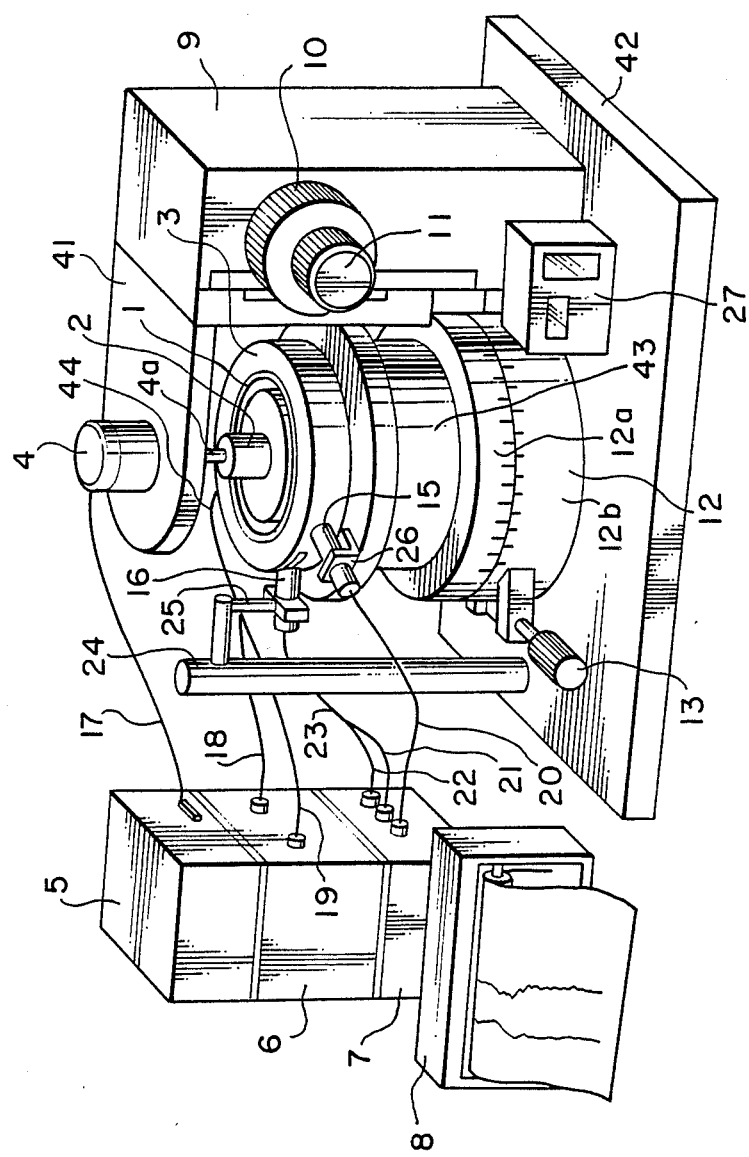
FIG. 1 is a perspective view of an apparatus for determining properties of cells according to an embodiment of the present invention.
Figure 2:
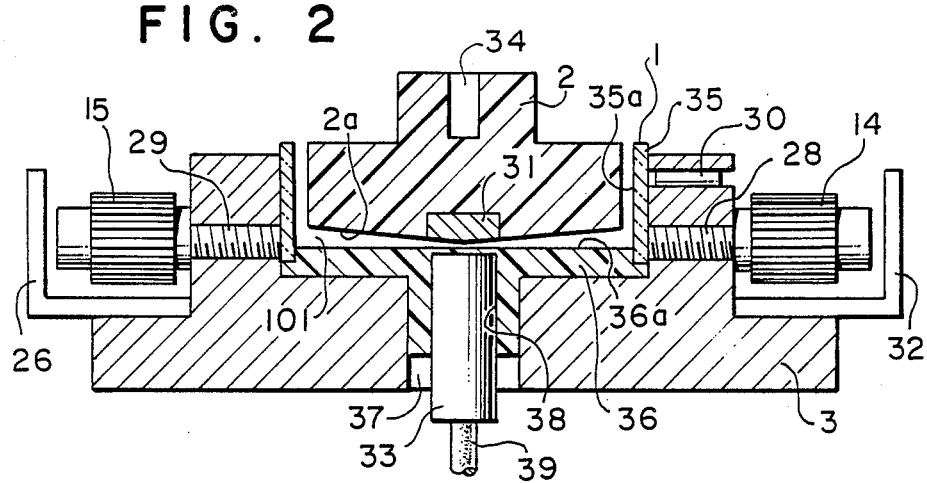
FIG. 2 is an enlarged partial vertical sectional view of the apparatus shown in FIG. 1.
Figure 3:
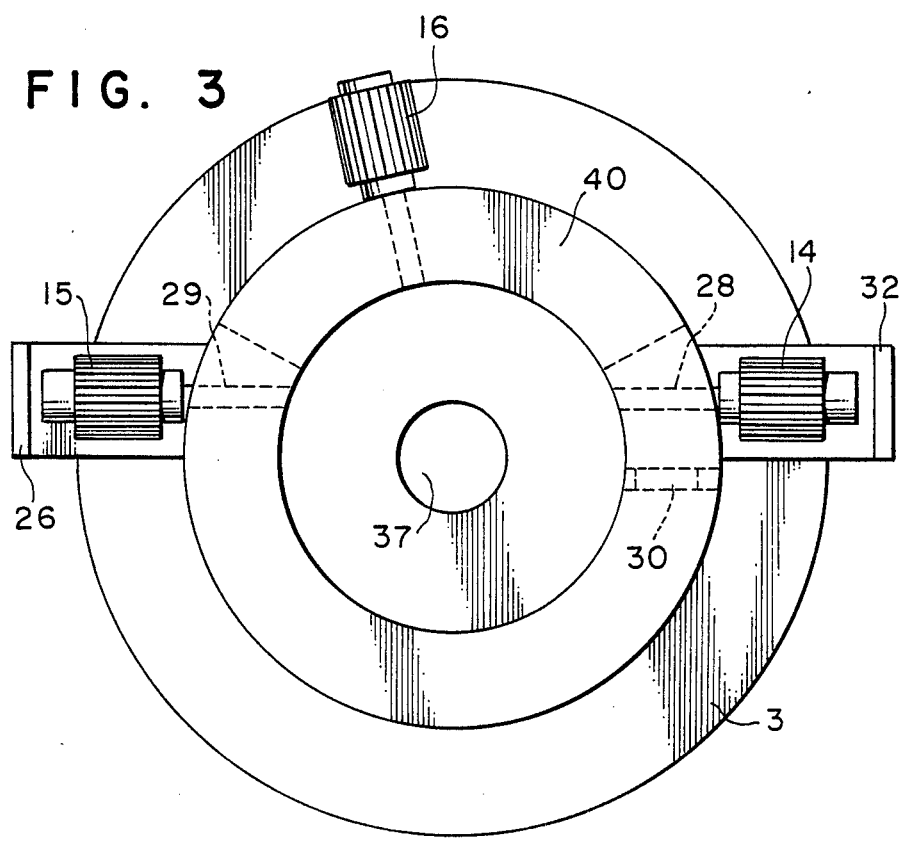
FIG. 3 is a plan view of the apparatus shown in FIG. 2 in a state that a rotor is removed.
Figure 4:
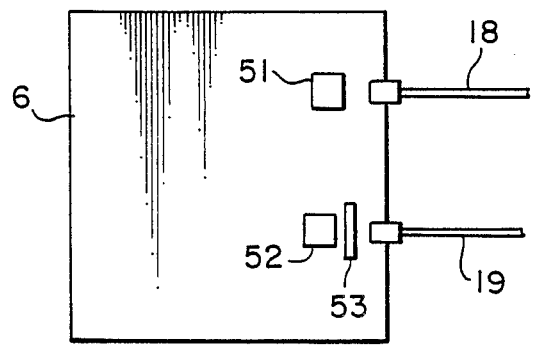
FIG. 4 is a schematic view of an inside of a light source unit of the apparatus shown in FIG. 1.
Figure 5:
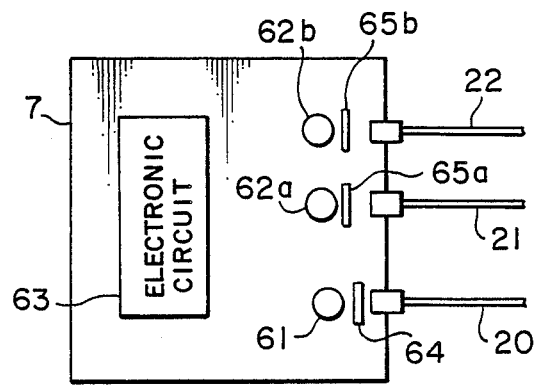
FIG. 5 is a schematic view of an inside of a photo detector unit of the apparatus shown in FIG. 1.

Some preferred embodiments of the present invention will be described hereunder with reference to the attached drawings.

FIGS. 1-5 illustrate an apparatus for determining functional properties of cells according to an embodiment of the present invention. This apparatus is designed particularly for determining properties of platelets in a sample of a platelet suspension.

In this embodiment, a sample containing chamber 101, which contains a sample of a platelet suspension as a sample of a cell suspension, is cylindrically defined by a cylindrical bath 1 having an inner bottom surface 36a and an inner side surface 35a. Bath 1 is constructed of a light-transmissible side wall 35 of a sufficiently polished transparent colerless acrylic resin and a non-light-transmissible bottom wall 36 which has a surface contacting the platelet suspension that is sufficiently polished and which is constructed from an acrylic resin. A recessed portion 38 is formed on the back side of bottom wall 36, and a sensor 33 of an eddy-current displacement gauge is disposed in the recessed portion.

A rotor 2 having a conical surface 2a with a convex shape in the direction toward inner bottom surface 36a is disposed in sample containing chamber 101. Rotor 2 is constructed from a non-light-transmissible acrylic resin, and its conical surface 2a is sufficiently polished. Conical surface 2a faces inner bottom surface 36a at an angle of not greater than 2°. A columnar stainless steel member 31 is formed of a magnetic material and is provided in rotor 2 at the bottom tip portion thereof, and the conical shaped surface of the member is sufficiently polished. A shaft hole 34 is formed in the upper portion of rotor 2, and an output shaft 4a of a coreless type D.C. motor 4 with an encoder is inserted into the shaft hole. Motor 4 is fixed to a fixing plate 41, and the fixing plate is attached to a height adjustable stage 9 mounted on a base plate 42. Height adjustable stage 9 has a rough adjustment dial 10 and a fine adjustment dial 11. A gap between rotor 2 and bottom wall 36 of bath 1 is adjusted by dials 10 and 11. The value of the gap is measured via sensor 33. Sensor 33 detects the position of columnar stainless steel member 31, the detected signal is sent to a display 27 provided on base plate 42 via cord 39 connected to the sensor and the display, and the value of the gap or the height of the rotor is displayed on the display. The bottom surface of columnar stainless steel member 31 may be partially or entirely a flat surface in order to make it easy to detect the position of the member by sensor 33. Motor 4 is driven according to a program stored in memory in a motor drive control unit 5.

Bath 1 is held in a recessed portion of a holder 3 constructed from stainless steel and the bath is fixed by a fixing pin 30 provided on the upper portion of the holder. A ray transmission path 28 is formed in holder 3 through the side wall of the holder at a position slightly above the inner bottom of the recessed portion of the holder. A transmitted ray detection path 29 is formed in holder 3 through the side wall of the holder at a position opposite to the position of ray transmission path 28. The path between ray transmission path 28 and transmitted ray detection path 29 is located away from the rotational center of rotor 2. A scattered transmission ray path 40 is provided in the side wall of holder 3 between ray transmission path 28 and transmitted ray detection path 29. Scattered ray transmission path 40 is formed as a slit extending in a circumferential direction about the side wall of holder 3. An optical fiber 14 is provided for ray transmission path 28 and an optical fiber 15 is provided for transmitted ray detection path 29. Each optical fiber is a single core type optical fiber the core of which consists of quartz glass and to which a plug of a FC type connector is connected. These optical fibers 14 and 15 are fixed to supports 32 and 26 via FC type connector adapters (not shown) attached to the supports, respectively. An optical fiber 16 for transmitting scattered rays is inserted into scattered ray transmission path 40. The core of this optical fiber 16 also consists of quartz glass and a plug of a FC type connector is connected to the optical fiber. Optical fiber 16 is fixed to a guide member 25 via a FC type connector adapter (not shown) and the guide member is supported by a stand 24 mounted on base plate 42.

Holder 3 is fixed on a bed 43, and the bed is mounted on a rotary table 12 which comprises an upper table 12a and a lower table 12b which can rotate and adjust the circumferential direction of the upper table by turning an adjusting dial 13 attached to the lower table. By this adjustment, the location of holder 3 is adjusted in its circumferential direction and the location of optical fiber 16 in scattered ray transmission path 40 is adjusted in the circumferential direction within the slit extension of the path in the circumferential direction. Namely, the angle for transmitting a scattered ray in the circumferential direction can be appropriately adjusted.

A multicore optical fiber 44 having on its end portion a plug of a FC type connector which is filled with twelve quartz optical fibers in a single ferrule is connected to support 32 to which the FC type connector adapter for fixing optical fiber 14 is attached. Multicore optical fiber 44 is divided to two multicore optical fibers 18 and 19 which have six fibers, respectively. An end portion of each of these multicore optical fibers 18 and 19 is also contained in a single ferrule, and is connected to a FC type connector adapter which is attached to a light source unit 6, via a plug of a FC type connector.

A He-Ne gas laser source 51 and an excitation light source 52 of a mercury-xenon lamp are assembled in light source unit 6. He-Ne gas laser source 51 is used for determining the aggregation of platelets. The laser source generates a gas laser ray the wave length of which is 632.8 nm, and it has an end-face output of 1.6 mW when a quartz optical fiber connected to it has a core with a diameter of 125 μm and a length of 2 m. Excitation light source 52 is used for determining the variation of the concentration of calcium ions in the cytoplasm of platelets, and it has an output of 100 W and an ultraviolet light transmissible filter 53 as an interference filter is attached to it.

One end of an optical fiber 20, which has plugs of a FC type connector at both ends, is connected to support 26 to which the FC type connector adapter for fixing optical fiber 15 is attached. A plug at another end of optical fiber 20 is connected to a FC type connector adapter provided on a photo detector unit 7. A multicore optical fiber 23 having on its end portion a plug of a FC type connector which is filled with twelve quartz optical fibers in a single ferrule is connected to optical fiber 16 which is fixed via guide member 25 and stand 25, via a FC type connector adapter attached to the guide member. Multicore optical fiber 23 is divided into two multicore optical fibers 21 and 22 which have six fibers, respectively. An end portion of each of these multicore optical fibers 21 and 22 is also contained in a single ferrule, and is connected to a FC type connector adapter which is attached to photo detector unit 7, via a plug of a FC type connector.

A photodiode 61, two photomultiplier tubes 62a and 62b and an electronic circuit 63 for receiving signals from these elements and analyzing data are assembled in photo detector unit 7. An intereference filter 64 the central wave length of which is 633 nm is attached to the FC type connector adapter to which optical filter 20 is connected, and the filter is connected to photodiode 61. An interference filter 65a the central wave length of which is 410 nm is provided in front of photomultiplier tube 62a and an interference filter 65b the central wave length of which is 480 nm is provided in front of photomultiplier tube 62b. These photomultiplier 62a and 62b are connected to the FC type connector adapters to which optical fibers 21 and 22 are connected, respectively, via these interference filters 65a and 65b, respectively.

A recorder 8 for receiving signals sent from photo detector unit 7 is connected to the photo detector unit, and the recorder continuously records data by means of two pens of the variation of the turbidity of the platelet suspension due to the aggregation of platelets and data of the variation of the concentration of the calcium ions in the platelets.

In this embodiment, holder 3 has a hole 37 at the central portion of its bottom wall because sensor 33 is built in bath 1. However, holder 3 may not have such a hole. Also, a sample containing chamber may be defined without a cylindrical bath, that is, by a holder itself.

The quantification measurement of the aggregation of platelets caused by applying a shear stress will now be explained. It is necessary to consider a certain index by generalizing an obtained aggregation curve of platelets in order to quantitatively estimate the status of the aggregation of the platelets. In the first conventional apparatus discussed above which is widely used for clinical examinations, the aggregation ratio (ARc) of platelets is defined as follows.

$$ARc\ (\%) = (I_t - I_{PRP})/(I_{PPP} - I_{PRP}) \times 100 \qquad (1)$$

In this equation, "$I_t$" is the amount of a transmitted ray when platelets aggregate, $I_{PPP}$ is the amount of a transmitted ray of platelet-poor plasma (hereinafter called "PPP"), and $I_{PRP}$ is the amount of a transmitted ray of platelet-rich plasma (hereinafter called "PRP") before platelets aggregate. This index greatly varies in accordance with the optical path length in the cells, the turbidity of the plasma and the number of platelets before aggregation. Moreover, since it is not proportional to the variation of the number of unaggregated platelets, it is not suitable for determining the aggregation of platelets. These problems are overcome by the apparatus according to the present invention, because the apparatus can detect the aggregation of platelets with a high sensitivity and therefore the difference between the amount of transmitted ray of "PPP" and the amount of transmitted ray of "PRP" becomes very large.

In the present invention, it is found that the relationship between the number of platelets and the amount of transmitted ray obeys Lambert Beer's law and that the variation of the amount of transmitted ray is caused primarily by the variation of the number of unaggregated platelets. Accordingly, the following equation is considered and defined as an index capable of showing an accurate aggregation ratio (ARi) of platelets.

$$ARi\ (\%) = \frac{\log(I_t/I_{PRP})}{\log(I_{PPP}/I_{PRP})} \times 100 \qquad (2)$$

It becomes possible to present the aggregation ratio of platelets as the variation of the number of unaggregated platelets and to quantitatively determine the aggregation of platelets regardless of the optical path length in the cells, the turbidity of the plasma and the number of platelets before aggregation, by using the above index.

EXAMPLE 1

Measurements are performed using the apparatus shown in FIG. 1 which has the following dimensions.

The radius of rotor 2 is 1.5 cm, the radius of columnar stainless steel member 31 is 2.5 mm, and the angle between conical surface 2a of the rotor and a plane perpendicular to the rotational axis of the rotor is 1.0°. The inner diameter of bath 1 is 3.1 cm, the outer diameter of the bath is 3.4 cm, and the depth of the bath into which a platelet suspension is introduced is 1.3 cm. The thickness of bottom wall 36 of bath 1 is 2 mm, and the thickness of the bottom portion at the position of hole 38 is 0.5 mm. The inner diameter of holder 3 is 3.41 cm and the outer diameter of the holder is 5.5 cm. Ray transmission path 28 and transmitted ray detection path 29 are located so that the distance between a linear path connecting the centers of the paths 28 and 29 and the center of the cylindrical recessed portion of holder 3 may be 0.8 cm. The slit of scattered ray transmission path 40 is formed so that the angle between the lines connecting the center of the recessed portion of holder 3 and the end surfaces of the slit in the circumferential direction of the holder may be 120°. The core diameter of optical fibers 14, 15, 16 and 20 is 1 mm, and their clad diameter is 1.035 mm. The core diameter of optical fibers 18, 19, 21, 22, 23 and 44 is 0.200 mm, and their clad diameter is 0.230 mm. The height of height adjustable stage 9 is 15.5 cm and the diameter of rotary table 12 is 9 cm. The length of base plate 42 is 20 cm and its width is 25 cm.

The operation of the apparatus and the process of the determination of the aggregate function of platelets in the platelet suspension will now be explained.

Blood is taken from a vein in the elbow of a healthy adult and placed into a plastic container via a siliconized 20 gauge needle at the rate of 3.8% sodium citrate aqueous solution/blood which equals 1/9. This blood is centrifugally separated at a centrifugal force of 100 G for fifteen minutes to obtain "PRP", and then, the remaining red cell suspension is centrifugally separated at the centrifugal force of 1500G for ten minutes to obtain "PPP". "PRP" which is adequately controlled in a number of platelets is made by using the obtained "PRP" and "PPP". This "PRP" controlled in a number of platelets is contained in the portion near bottom wall 36 of bath 1 by 0.3 ml, rotor 2 is downwardly moved above the bottom wall by turning rough adjustment dial 10 and fine adjustment dial 11 of height adjustable stage 9, and the gap between columnar stainless steel member 31 and the center of bottom wall 36 is set to 40 μm by detecting the gap by sensor 33 and by displaying the gap on display 27. Then, rotor 2 is rotated, a shear stress is applied to the contained "PRP" within the range of 0–200 dyne/cm$^2$ for five minutes, a ray with the wave length of 633 nm is continuously projected into the sample from optical fiber 14 and the transmitted ray through the sample is received via optical fiber 15 and detected by photo detector unit 7. As platelets aggregate, the amount of transmittance increases, and its variation is recorded by recorder 8.

Figure 6:
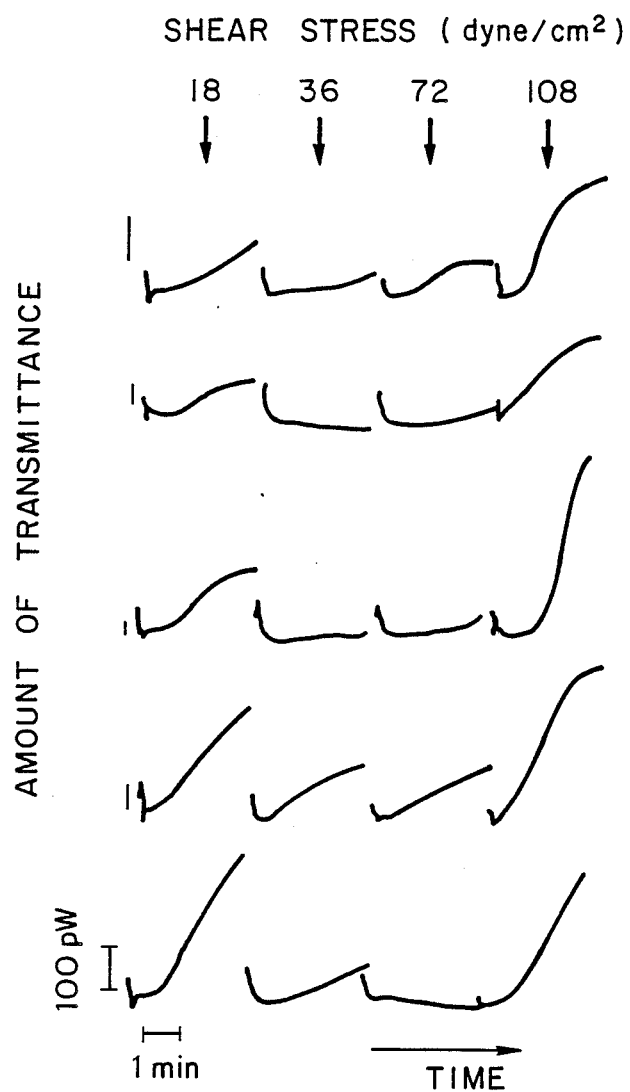
FIG. 6 is a graph showing amounts of transmittance measured in Example 1 using the apparatus shown in FIG. 1.

FIG. 6 show aggregation curves of platelets of five healthy adults when shear stresses of 18 dyne/cm$^2$, 36 dyne/cm$^2$, 72 dyne/cm$^2$ and 108 dyne/cm$^2$ are applied. From FIG. 5, it is understood that the aggregation of platelets is generally promoted at the shear stresses of 18 dyne/cm$^2$ and 108 dyne/cm$^2$ in comparison with the shear stresses of 36 dyne/cm$^2$ and 72 dyne/cm$^2$.

EXAMPLE 2

The same apparatus as in Example 1 is used. The following samples are measured with respect to the aggregation of plateles at the shear stresses of 18 dyne/cm$^2$ and 108 dyne/cm$^2$, in a manner similar to in Example 1.

Figure 7A:
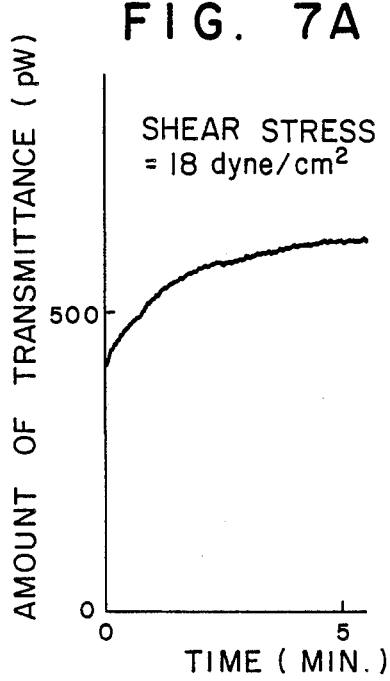
FIGS. 7A and 7B are graphs showing amounts of transmittance measured in Example 2 using the apparatus shown in FIG. 1.
Figure 7B:
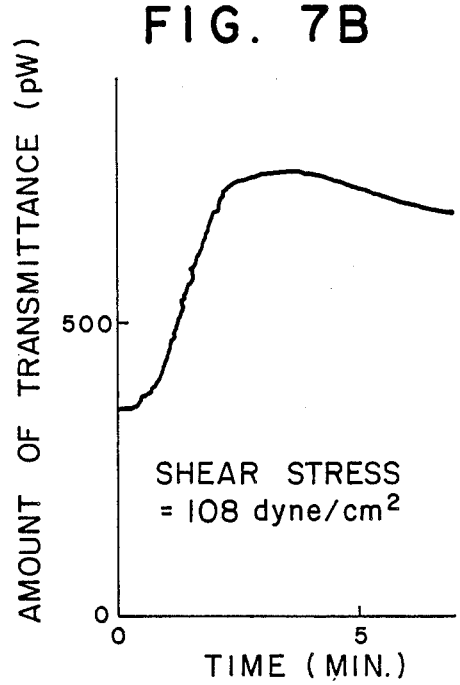
Figure 8A:
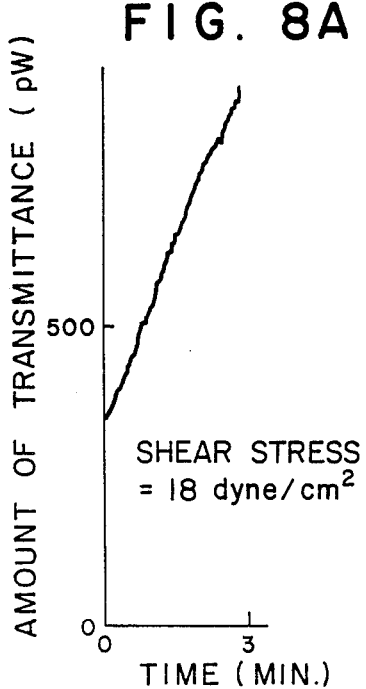
FIGS. 8A and 8B are graphs showing further amounts of transmittance measured in Example 2 using the apparatus shown in FIG. 1.
Figure 8B:
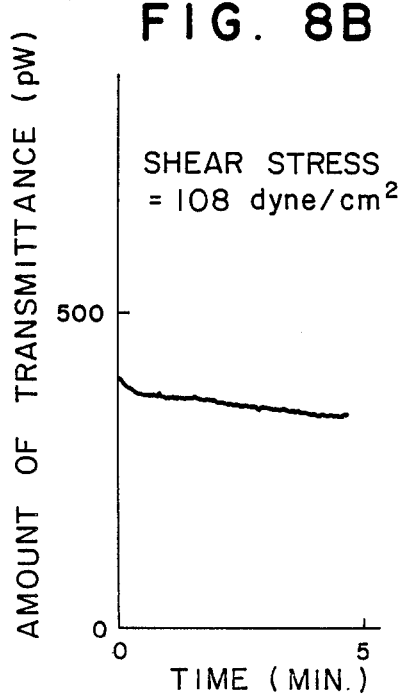
Figure 10B:
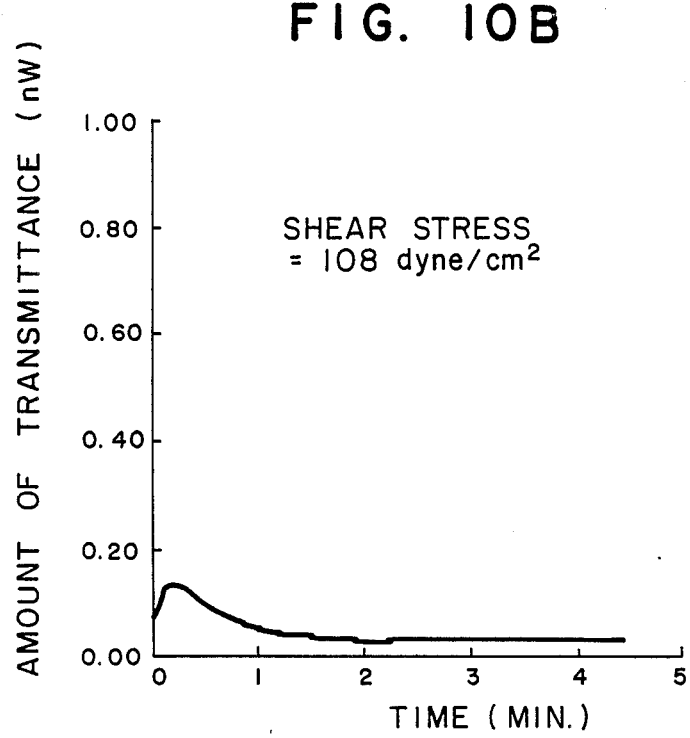
Figure 11:
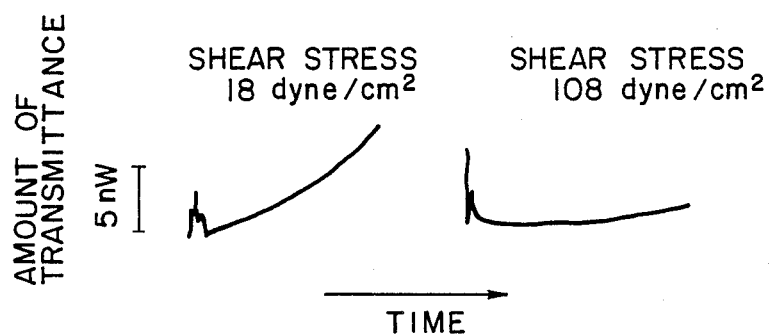
FIGS. 11-14 are graphs showing further amounts of transmittance measured in Example 2 using the apparatus shown in FIG. 1.
Figure 12:
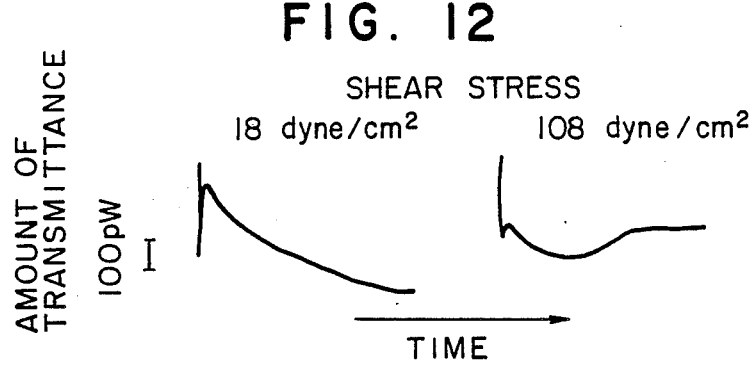
Figure 13:
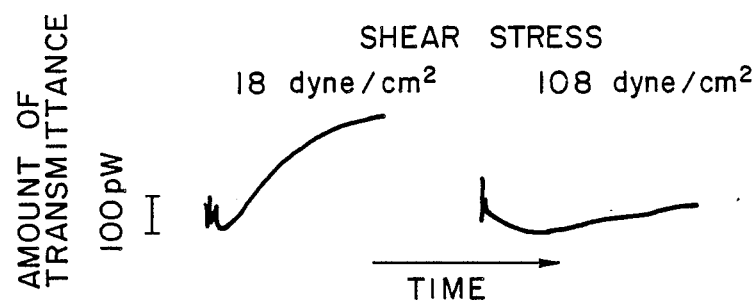
Figure 14:
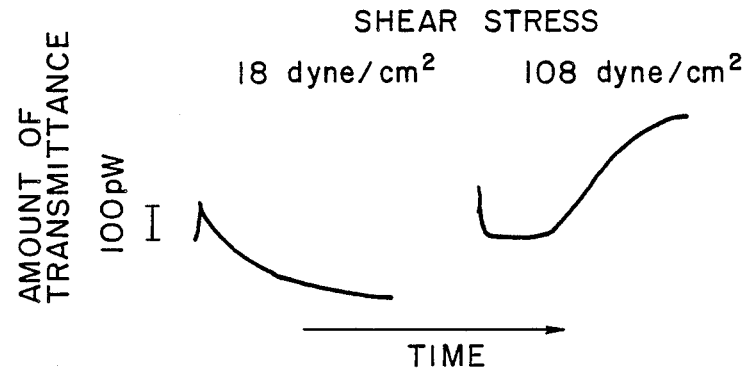

FIGS. 7A and 7B show the result of Sample No. 1 of a normal platelet suspension. FIGS. 8A and 8B show the result of Sample No. 2 of a platelet suspention whose glycoprotein GPIb, which is closely connected with the adhesive properties of platelets exhibited by the cell membrane of platelets, is treated with monoclonal antibody. FIGS. 9A and 9B show the result of Sample No. 3 of a platelet suspension whose GPIIb-/IIIa, which is closely connected with the aggregation properties of platelets exhibited by the cell membrane of platelets, is treated with monoclonal antibody. FIGS. 10A and 10B show the result of Sample No. 4 of a platelet suspension whose von Willebrand factor, which is connected with the adhesive properties of platelets, is treated with monoclonal antibody FIG. 11 shows the result of Sample No. 5 of a platelet suspension which is taken from a patient suffering from Bernard-Soulier syndrome in which GPIb is lacking. FIG. 12 shows the result of Sample No. 6 of a platelet suspension which is taken from a patient suffering from thrombasthenia in which GPIIb/IIIa is lacking. FIG. 13 shows the result of Sample No. 7 of a platelet suspension which is taken from a patient suffering from von Willebrand disease in which von Willebrand factor is lacking. FIG. 14 shows the result of Sample No. 8 of a platelet suspension which is taken from a patient suffering from afibrinogenemia in which fibrinogen is lacking.

With Sample No. 2 as shown in FIGS. 8A and 8B as compared with Sample No. 1 shown in FIGS. 7A and 7B, the aggregation of platelets is promoted at the low shear stress of 18 dyne/cm², and it is completely suppressed at the high shear stress of 108 dyne/cm². With Sample No. 3 as shown in FIGS. 9A and 9B, the aggregation of platelets is completely suppressed at the low shear stress of 18 dyne/cm², and it is slightly exhibited at the high shear stress of 108 dyne/cm². With Sample 4 as shown in FIGS. 10A and 10B, the aggregation of platelets is not suppressed at the low shear stress of 18 dyne/cm², but it is almost completely suppressed at the high shear stress of 108 dyne/cm². With Sample No. 5 as shown in FIG. 11, the platelets normally aggregate at the low shear stress of 18 dyne/cm², but the platelets do not aggregate at all at the high shear stress of 108 dyne/cm². With Sample No. 6 as shown in FIG. 12, the platelets do not aggregate at all at the low shear stress of 18 dyne/cm², but the platelets slightly aggregate at the high shear stress of 108 dyne/cm². With Sample No. 7 as shown in FIG. 13, the platelets normally aggregate at the low shear stress of 18 dyne/cm², but the platelets do not aggregate at all at the high shear stress of 108 dyne/cm². With Sample No. 8 as shown in FIG. 14, the platelets do not aggregate at all at the low shear stress of 18 dyne/cm², but the platelets normally aggregate at the high shear stress of 108 dyne/cm².

As is evident from the above results, the abnormality caused by GPIb, GPIIb/IIIa, fibrinogen and von Willebrand factor which are closely connected with functions and properties of platelets is easily examined by examining the aggregation of platelets in low and high shear stress ranges.

EXAMPLE 3

In the apparatus of Example 1, an instrumentation system comprising a photo counter, a GP-IB interface and a microcomputer is connected to two photomultipliers 62a and 62b. The variation of the concentration of calcium ions in the platelets is determined.

First, a buffer solution of a calcium ion solution is made as follows. A solution, which comprises 60 mM ethyleneglycol-bis(β-aminoethylether)-N,N,N',N'-tetraacetate (hereinafter called "EGTA") and 12 mM 3-morpholinopropanesulfonic acid (hereinafter called "MOPS"), is added to a solution which comprises 120 mM potassium chloride (hereinafter called "KCl"), 12 mM MOPS and 12 mM calcium chloride (hereinafter called CaCl₂). While it is confirmed that calcium ion has not been detected by a calcium ion electrode, a solution with an adjusted pH of 7.20 is made which comprises 100 mM KCl, 10 mM MOPS and 10 mM EGTA calcium salt (hereinafter called "K₂Ca EGTA"). A solution comprising 60 mM EGTA and 12 mM MOPS is added to a solution comprising 120 mM KCl and 12 mM MOPS by 1/5 in volume, and a solution with pH 7.20 is adjusted which comprises 100 mM KCl, 10 mM MOPS and 10 mM EGTA potassium salt (hereinafter called "K₂H₂ EGTA"). Using these two kinds of solutions, buffer solutions of calcium ion having concentrations of 0 mM, 37.3×10⁻⁶ mM (37.3 nM), 100×10⁻⁶ mM (100 nM), 226×10⁻⁶ mM (226 nM), 604×10⁻⁶ mM (604 nM) and 1 mM are made.

Next, an aqueous solution of Indo-1, which is a pigment that emits a specific fluorescence upon combining with calcium ion, is added to the above buffer solutions in amounts with respect to calcium ion concentrations of 6/1000 in volume, respectively. In this way the samples are made.

Each sample of 0.3 ml is contained in bath 1 and rotor 2 is moved downward in a similar manner as in Example 1. Rotor 2 is rotated and a ultraviolet ray is projected into the sample via optical fiber 14. Indo-1 emits two types of fluorescence at different wave lengths upon exposure to the ultraviolet ray, that is, a fluorescence with a wave length of 410 nm emitted from the Indo-1 combined with the calcium ion and a fluorescence with a wave length of 480 nm emitted from Indo-1 alone. These fluorescence emissions are measured via the above-mentioned instrumentation system.

With respect to the relationship between the concentration of calcium ion and the strength of the above fluorescence emissions, the aforementioned document of Grynkiewicz et al. reports the following equation.

$$Ca^{2+} = Kd\ (S_{indo-1}^{480}/S_{indo-1Ca}^{480})$$
$$(R - Rmin)/(Rmax - R)$$

In this equation, $Ca^{2+}$ is the concentration of calcium ion. Kd is a calcium ion dissociation constant of Indo-1 combined with calcium ion. $S_{indo-1}^{480}$ is the strength of fluorescence with a wave length of 480 nm when the concentration of calcium ion is zero. $S_{indo-1Ca}^{480}$ is the strength of fluorescence with a wave length of 480 nm when all of Indo-1 is combined with the calcium ions by increasing the calcium ion concentration to an excessive amount (corresponding a buffer solution the concentration of calcium ion of which is 1 mM). Rmin is the fluorescent strength ratio of the fluorescence emissions with wave lengths of 410 nm and 480 nm when the concentration of calcium ion is zero. Rmax is the fluorescent strength ratio of the fluorescence emissions with wave lengths of 410 nm and 480 nm when the calcium ion concentration is adjusted to an excessive amount. R is the fluorescent strength ratio of the fluorescence emissions with wave lengths of 410 nm and 480 nm when the fluorescence of each calcium ion buffer solution is determined. The fluorescent strength ratio R of each sample is substituted in the above equation, Kd is determined and a calibration curve is drawn.

Then, a sample of a platelet suspension is made as follows.

First, "PRP" is made by taking blood from a healthy adult in the same manner as in Example 1. Acid citrate dextrose is added to this "PRP" so as to make the final concentration 20%, and it is centrifugally separated with a centrifugal force of 800 G for seven minutes to cause sedimentation of the platelets. After the supernatant is removed, HEPES-Tyrode buffer solution, which comprises 4 mM 4-(2-hydroxyethyl)piperazine-1-ethanesulfuric acid, 137 mM sodium chloride, 2.7 mM potassium chloride, 3.3 mM sodium phosphate, 1 mM magnesium chloride, 5.6 mM glucose and 0.35 mg/ml bovine serum albumin, is added to adjust the number of platelets to 10×10⁴/μl. Further, to this platelet suspension is added a dimethylsulfoxide solution of 1 mM Indo-1AM, which exhibits permeability through cell membrane by acetoxymethylesterificating the carboxyl group of the above-described Indo-1, so as to adjust the final concentration of the Indo-1AM to 5 μM. The resulting suspension is left for thirty minutes at 37° C. Acid citrate dextrose is added to this platelet suspension so as to adjust its final concentration to 20%, and the suspension is centrifugally separated with a centrifugal force of 800 G for seven minutes to cause sedimentation of platelets again. After the supernatant is eliminated, HEPES-Tyrode buffer solution is added to adjust the number of platelets to 10×10⁴/μl. Thus the sample for determining the concentration of calcium ion in platelets is made.

Figure 15:
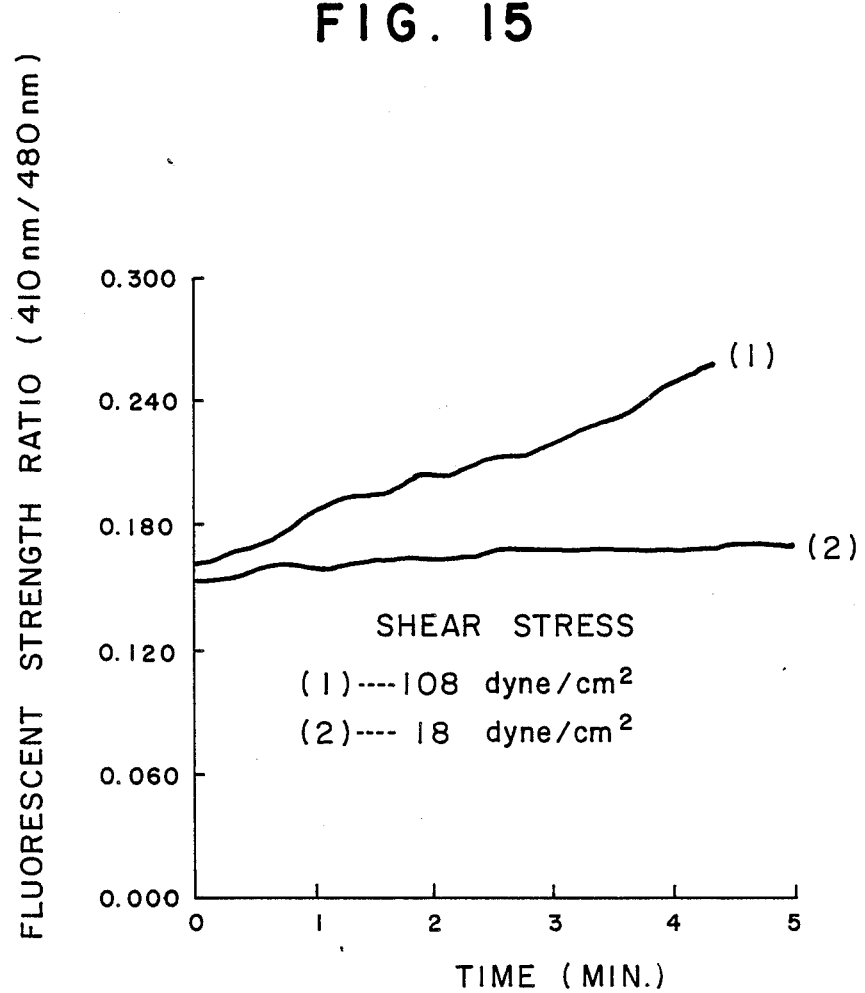
FIG. 15 is a graph showing fluorescent strength ratio measurements obtained in Example 3 using the apparatus shown in FIG. 1.

Fibrinogen and von Willebrand factor are added to the sample so as to adjust their final concentration to 20 $\mu$g/ml, respectively. The sample of 0.3 ml is placed into bath 1, and the fluorescent strength is determined by a process similar to that above for making the aforementioned calibration curve. FIG. 15 shows the variation of the fluorescent strength ratio R of the fluorescense emissions with wave lengths of 410 nm and 480 nm at the shear stress conditions of 18 dyne/cm$^2$ and 108 dyne/cm$^2$. As is evident from FIG. 15, the concentration of calcium ion in the platelets does not vary in the low range of shear stress, but it increases in the high range of shear stress.

EXAMPLE 4

In the apparatus of Example 1, an instrumentation system comprising a photo power meter, a GP-IB interface and a microcomputer is connected to photodiode 61. The aggregation of platelets is determined and expressed by the new index shown by equation (2).

Figure 16:
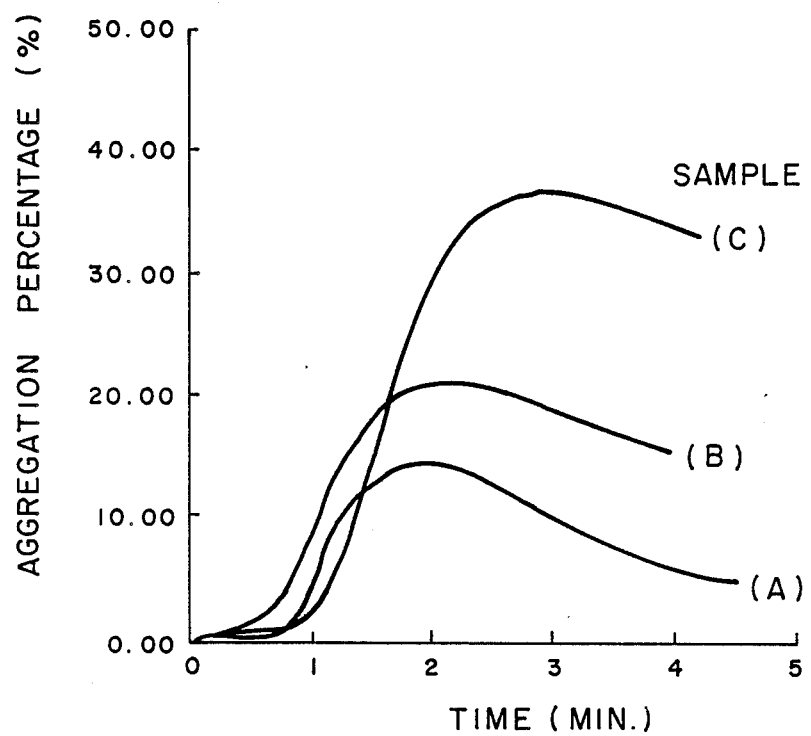
FIG. 16 is a graph showing aggregation percentage measurements of platelets obtained in Example 4, measured by a coventional calculation method.
Figure 17:
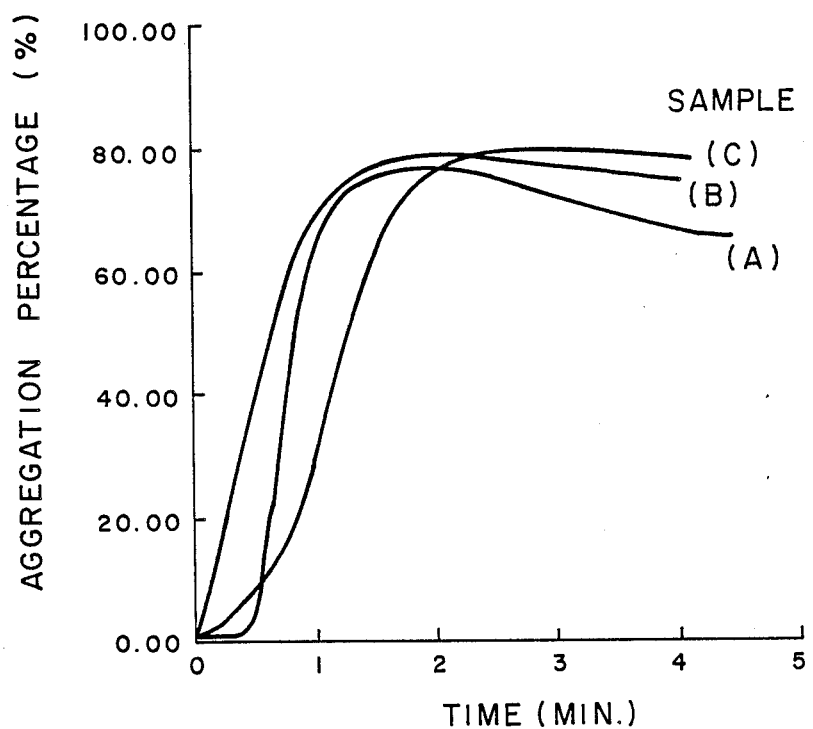
FIG. 17 is a graph showing aggregation percentage measurements of platelets obtained in Example 4, measured by a calculation method according to the present invention.

First, a tube constructed from vinyl chloride and having an outer diameter of 1.35 mm is inserted into a carotid of a rabbit whose weight is about 3 kg. The blood is taken from the rabbit into a plastic container at the rate of 3.8% sodium citrate aqueous solution/blood which equals 1/9. Then, "PPP" and "PRP" are made in the same manner as in Example 1, and platelet suspensions for Sample A in which the number of platelets is $42 \times 10^4/\mu$l, Sample B in which the number of platelets is $21 \times 10^4/\mu$l and Sample C in which the number of platelets is $14 \times 10^4/\mu$l are made by diluting the "PRP" with the "PPP". At first a shear stress of 3 dyne/cm$^2$ is applied to these Samples for fifteen minutes so as not to cause the aggregation of platelets, and the transmittance through the "PRP" before the aggregation of platelets is determined. Then, the shear stress is increased to 18 dyne/cm$^2$ for fifteen minutes, and the data of the aggregation of platelets is obtained. The transmittance is determined, the aggregation curve of platelets, which is represented by aggregation percentage, is calculated using the microcomputer, and the maximum aggregation percentage is also calculated. FIG. 16 shows the curves according to a conventional calculation method, that is, obtained from equation (1) aforementioned. FIG. 17 shows the curves according to the new method of the present invention, that is, obtained from equation (2).

Further, immediately after the above determination, the respective platelets are fixed by formalin, the number of unaggregated platelets are counted by an automatic platelet counter, and the variation rate of the number of platelets between the numbers before and after aggregation is calculated. As a result, the calculated rate of Sample A is 65%, that of Sample B is 76% and that of Sample C is 80%. These values correlate well with the aggregation percentages of respective Samples which are obtained from the curves shown in FIG. 17.

On the other hand, in the conventional determination method as is evident from FIG. 16, the aggregation percentages at the termination of the measurement, obtained from the aggregation curves, are greatly lower than the values obtained by the automatic platelet counter. Moreover, when the aggregation percentage is represented by the conventional method, an illusory conclusion may be drawn that the smaller the number of platelets existing before aggregation, the more actively promoted is the aggregation of platelets.

As described above, the aggregation rate calculated from equation (2) can accurately and quantitatively indicate the aggregation of platelets.

Although several preferred embodiments of the present invention have been described in detail, it will be appreciated by those skilled in the art that various modifications and alterations can be made to the particular embodiments shown without materially departing from the novel teachings and advantages of this invention. Accordingly, it is to be understood that all such modifications and alterations are included within the scope of the invention as defined by the following claims.

What is claimed is:

1. An apparatus for determining the functioning properties of cells which are contained in a sample of a cell suspension comprising:
   (a) a sample containing chamber cylindrically defined by an inner bottom surface and an inner side surface for containing a sample therein;
   (b) a rotor disposed in said sample containing chamber and having a conical surface with a convex shape in the direction toward said inner bottom surface of said sample containing chamber, said conical surface facing said inner bottom surface at an angle of not greater than 2°;
   (c) a ray transmission path provided on said inner side surface of said sample containing chamber for transmitting a ray through said sample located between said inner bottom surface of said sample containing chamber and said conical surface of said rotor; and
   (d) a transmitted ray detection path provided on said inner side surface of said sample containing chamber opposite to said ray transmission path for receiving a ray transmitted through said sample located between said inner bottom surface of said sample containing chamber and said conical surface of said rotor, wherein an optical path is defined through said sample between said ray transmission path and said transmitted ray detection path so as to have an optical path length of not smaller than 1 cm.

2. The apparatus according to claim 1 further comprising:
   (e) a driving means connected to said rotor for rotating said rotor;
   (f) a control unit for controlling said driving means;
   (g) a light source unit operatively connected to said ray transmission path for supplying rays to said ray transmission path;
   (h) a photo detector unit operatively connected to said transmitted ray detection path for detecting transmittance from said transmitted ray detection path; and
   (i) a recorder connected to said photo detector unit for recording a signal sent from said photo detector unit.

3. The apparatus according to claim 1 further comprising a scattered ray transmission path provided on said inner side surface of said sample containing chamber.

4. The apparatus according to claim 1, wherein said sample containing chamber is defined by a cylindrical bath constructed of a light-transmissible side wall and a bottom wall.

5. The apparatus according to claim 4, wherein said bottom wall is non-light-transmissible.

6. The apparatus according to claim 1, wherein said cell suspension is a platelet suspension.

7. The apparatus according to claim 1, wherein the distance between said inner bottom surface of said sample containing chamber and said conical surface of said rotor is adjustable.

8. The apparatus according to claim 7, wherein at least the tip portion of said conical surface of said rotor is constructed from a magnetic material, a sensor of an eddy-current displacement gauge is provided in a bottom wall of said sample containing chamber, and said distance is detected by said sensor.

9. The apparatus according to claim 1, wherein said angle between said conical surface and said inner bottom surface is in the range of $0.3°-1.5°$.

10. The apparatus according to claim 1, wherein said optical path length is in the range of 1-4 cm.

11. The apparatus according to claim 1, wherein said ray is introduced into said ray transmission path via an optical fiber.

12. The apparatus according to claim 1, wherein said transmitted ray is received by said transmitted ray detection path via an optical fiber.

13. The apparatus according to claim 2, wherein said driving means comprises a direct current motor with an encoder.

14. The apparatus according to claim 2, wherein said control unit is programed for changing the rotational speed of said driving means.

15. The apparatus according to claim 2, wherein an interference filter is attached to said light source unit.

16. The apparatus according to claim 2, wherein said light source unit includes a light source which emits a monochromatic light.

17. The apparatus according to claim 2, wherein said photo detector unit has a photoelectromotive element which utilizes photoelectromotive force.

18. The apparatus according to claim 17, wherein said photoelectromotive element is a photodiode.

19. The apparatus according to claim 2, wherein said photo detector unit has a photomultiplier tube.

20. The apparatus according to claim 3, wherein said scattered ray transmission path is formed as a slit extending on said inner side surface of said sample containing chamber in a circumferential direction about said inner side surface.

21. The apparatus according to claim 20, wherein an optical fiber is provided in said scattered ray transmission path for receiving and transmitting scattered rays emitted from said sample.

22. The apparatus according to claim 21, wherein the location of said optical fiber in said scattered ray transmission path is adjustable by turning said sample containing chamber in a circumferential direction with respect to said inner side surface.

23. A method for determining the functioning properties of cells which are contained in a sample of a cell suspension, comprising the steps of:
(a) placing a sample into a sample containing chamber which is cylindrically defined by an inner bottom surface and an inner side surface;
(b) applying a shear stress onto said sample which is located between said inner bottom surface of said sample containing chamber and a conical surface of a rotor disposed in said sample containing chamber by rotating said rotor, said conical surface having a convex shape in the direction toward said inner bottom surface and facing said inner bottom surface at an angle of not greater than 2°;
(c) projecting a ray from said inner side surface along an optical path through said sample located between said conical surface and said inner bottom surface so as to maintain an optical path length in said sample at a length of not smaller than 1 cm;
(d) detecting transmittance through said sample from said inner side surface;
(e) determining the degree of aggregation of said cells contained in said sample, which is caused by applying said shear stress, by measuring the variation of said transmittance from said inner side surface.

24. The method according to claim 23, wherein said cell suspension is a platelet suspension.

25. The method according to claim 24, wherein said shear stress is applied in the range of 10-40 dyne/cm$^2$ and aggregation properties of platelets are determined by measuring the variation of said transmittance.

26. The method according to claim 24, wherein said shear stress is applied both in the ranges of 10-40 dyne/cm$^2$ and not smaller than 80 dyne/cm$^2$, and aggregation properties and adhesive properties of the platelets are determined by measuring the variation of said transmittance.

27. The method according to claim 24 further comprising the steps of:
adding to said sample a pigment which emits a fluorescence upon combination with calcium ions in the cytoplasm of platelets contained in said platelet suspension;
projecting a ray into said sample, said ray containing an excitation wave length for said pigment;
detecting the fluorescence emitted from said pigment which is generated by said excitation wave length; and
determining the variation of the concentration of said calcium ions by measuring the variation of said detected fluorescence.

* * * * *